(12) United States Patent
Kang et al.

(10) Patent No.: US 10,149,652 B2
(45) Date of Patent: Dec. 11, 2018

(54) ENDOSCOPE SYSTEM FOR DIAGNOSIS SUPPORT AND METHOD FOR CONTROLLING SAME

(71) Applicants: DAEGU GYEONGBUK INSTITUTE OF SCIENCE AND TECHNOLOGY, Daegu (KR); KONKUK UNIVERSITY INDUSTRIAL COOPERATION CORP, Seoul (KR)

(72) Inventors: Won Seok Kang, Daegu (KR); Che Il Moon, Daegu (KR); Jin Kook Kim, Seoul (KR)

(73) Assignees: Daegu Gyeongbuk Institute of Science and Technology, Daegu (KR); Konkuk University Glocal Industry-Academic Collaboration Foundation, Chuncheongbuk-Do (KR)

( * ) Notice: Subject to any disclaimer, the term of this patent is extended or adjusted under 35 U.S.C. 154(b) by 463 days.

(21) Appl. No.: 14/779,688

(22) PCT Filed: Oct. 10, 2013

(86) PCT No.: PCT/KR2013/009051
§ 371 (c)(1),
(2) Date: Sep. 24, 2015

(87) PCT Pub. No.: WO2014/157796
PCT Pub. Date: Oct. 2, 2014

(65) Prior Publication Data
US 2016/0073958 A1    Mar. 17, 2016

(30) Foreign Application Priority Data
Mar. 26, 2013  (KR) ........................ 10-2013-0032392

(51) Int. Cl.
A61B 1/00 (2006.01)
A61B 5/00 (2006.01)
(Continued)

(52) U.S. Cl.
CPC .......... *A61B 5/6852* (2013.01); *A61B 1/0002* (2013.01); *A61B 1/00009* (2013.01);
(Continued)

(58) Field of Classification Search
CPC ............ A61B 1/00009; A61B 1/00016; A61B 1/0002; A61B 1/00105; A61B 1/04;
(Continued)

(56) References Cited

U.S. PATENT DOCUMENTS 5,839,438 A * 11/1998 Graettinger ......... G06F 19/3487
128/904
2002/0029157 A1* 3/2002 Marchosky ........... G06F 19/322
705/3

(Continued)

FOREIGN PATENT DOCUMENTS

JP  2007-143751 A  6/2007
KR  10-2009-0099446 A  9/2009
(Continued)

OTHER PUBLICATIONS

International Search Report of PCT/KR2013/009051 dated Mar. 26, 2013.
Korean Office Action No. 10-2013-0032392.

*Primary Examiner* — John P Leubecker
(74) *Attorney, Agent, or Firm* — Eversheds Sutherland (US) LLP

(57) ABSTRACT

An endoscope system for diagnosis support and a method for controlling the same. An endoscope module and an endoscope adaptor module are capable of taking images in the body and further measuring the temperature, humidity,
(Continued)

volume and air flow in the body. According to the images, temperature, humidity, volume and air flow in the body, an auxiliary diagnosis module may diagnose suspected diseases in the body and may display, to the outside, a disease diagnosis list for the suspected diseases in the body.

8 Claims, 6 Drawing Sheets

(51) Int. Cl.
*A61B 5/01* (2006.01)
*A61B 1/04* (2006.01)
*A61B 5/087* (2006.01)
*G16H 50/20* (2018.01)
*A61B 5/107* (2006.01)
*G06F 19/00* (2018.01)

(52) U.S. Cl.
CPC ...... *A61B 1/00016* (2013.01); *A61B 1/00045* (2013.01); *A61B 1/00105* (2013.01); *A61B 1/00112* (2013.01); *A61B 1/04* (2013.01); *A61B 5/01* (2013.01); *A61B 5/087* (2013.01); *A61B 5/7267* (2013.01); *A61B 5/7282* (2013.01); *G06F 19/00* (2013.01); *G16H 50/20* (2018.01); *A61B 1/00052* (2013.01); *A61B 5/1076* (2013.01); *A61B 2562/029* (2013.01); *G06F 19/321* (2013.01)

(58) Field of Classification Search
CPC ........... A61B 1/227; A61B 1/233; A61B 1/24; A61B 5/7282; A61B 5/7264; A61B 5/7267; A61B 5/0024; G06F 19/345; G06F 19/3406; G06F 19/34
See application file for complete search history.

(56) References Cited

U.S. PATENT DOCUMENTS

| | | | |
|---|---|---|---|
| 2004/0193029 A1 | 9/2004 | Glukhovsky | |
| 2006/0184473 A1* | 8/2006 | Eder | G06N 5/022 706/20 |
| 2007/0015989 A1* | 1/2007 | Desai | A61B 1/00009 600/407 |
| 2008/0104116 A1* | 5/2008 | Van Hoe | G06K 9/6267 |
| 2008/0171916 A1* | 7/2008 | Feder | G06F 19/3443 600/300 |
| 2009/0203986 A1* | 8/2009 | Winnick | A61B 1/227 600/407 |
| 2010/0272338 A1* | 10/2010 | Agnihotri | G06F 19/321 382/131 |
| 2010/0298895 A1 | 11/2010 | Ghaffari et al. | |
| 2011/0043612 A1* | 2/2011 | Keller | A61B 1/00165 348/49 |
| 2011/0301414 A1* | 12/2011 | Hotto | A61B 1/00009 600/114 |
| 2013/0096457 A1* | 4/2013 | Qiu | A61B 1/267 600/549 |
| 2013/0245417 A1* | 9/2013 | Spector | A61B 5/0013 600/407 |
| 2014/0122109 A1* | 5/2014 | Ghanbari | G06F 19/363 705/2 |
| 2014/0155763 A1* | 6/2014 | Bruce | A61B 5/7221 600/484 |
| 2014/0257058 A1* | 9/2014 | Clarysse | G06Q 50/22 600/301 |
| 2014/0378810 A1* | 12/2014 | Davis | G06T 5/40 600/407 |
| 2015/0164340 A1* | 6/2015 | Bedingham | A61B 7/04 600/484 |
| 2015/0182143 A1* | 7/2015 | Hirata | A61B 5/055 600/408 |
| 2016/0110389 A1* | 4/2016 | Oltman | G06F 17/30342 707/736 |
| 2017/0319145 A1* | 11/2017 | Pipke | A61B 5/0205 |

FOREIGN PATENT DOCUMENTS

KR 10-2011-0130288 A 12/2011
KR 10-2012-0114895 A 10/2012

* cited by examiner

ENDOSCOPE SYSTEM FOR DIAGNOSIS SUPPORT AND METHOD FOR CONTROLLING SAME

TECHNICAL FIELD

Embodiments relate to a diagnosis assisting endoscope system and a controlling method of the diagnosis assisting endoscope system, and more particularly, to a diagnosis assisting endoscope system and a controlling method of the diagnosis assisting endoscope system that may accurately diagnose suspected diseases of an inspection target by taking an image of a body and by measuring a temperature, a humidity, a volume, and an airflow of the body in the case of performing endoscopy, and may effectively assist an endoscopic diagnosis by providing the suspected diseases of the inspection target in real time.

RELATED ART

In general, endoscopy refers to looking inside the body, for example, to examining the interior of a hollow organ or cavity of the body, for medical reasons using an endoscope. The endoscopy may examine the inside of the body without performing a medical procedure such as laparotomy or a surgical operation and thus, is widely used to diagnose diseases in the medical field.

An endoscope device refers to a medical examining device that is inserted into the body and performs endoscopy. The endoscope device may include, for example, a bronchoscope, an esophagoscope, a gastroscope, a laparoscope, and a rectoscope. Also, the endoscope device may be classified into one for verifying the inspection target with naked eyes, one for viewing an image transferred by glass fiber, and one for taking a photo of the inspection target, based on a method of verifying the inspection target.

The endoscope device according to the related art is generally configured to provide only an image of the inspection target in the body. Accordingly, to enhance the diagnostic performance, technology for accurately acquiring a high resolution image is applied to the endoscope device according to the related art. For example, an endoscope device for improving a lesion discrimination capacity using light of a visible band and a near infrared band is disclosed in Korean Patent Publication No. 10-2012-0114895 titled "endoscope apparatus and image acquisition method of the endoscope, published on Oct. 17, 2012.

Meanwhile, technology for assisting a diagnosis of disease in the case of performing endoscopy has also been partially developed. For example, a method of diagnosing a disease by analyzing an ultrasonic endoscopic image of submucosal tumor to standardize an image acquired through endoscopic ultrasonography and to use the standardized image for materials for an objective disease diagnosis is disclosed in Korean Patent Registration No. 10-1118211 titled "diagnosis of submucosal tumor using endoscopic ultrasonic image analysis", registered on Feb. 13, 2012.

However, there were some constraints in diagnosing a disease only with an image of an affected area, for example, lesion. That is, it is difficult to accurately diagnose various types of diseases only with image verification about the affected area of the body. Due to such diagnostic ambiguity, a clinic time may increase. Further, in the case of performing endoscopy, a disease associated with the inspection target may be diagnosed fully depending on the judgment of a doctor. Accordingly, an error and a misdiagnosis are highly likely to occur.

SUBJECTS

Embodiments provide a diagnosis assisting endoscope system and a controlling method of the diagnosis assisting endoscope system that may measure an image, a temperature, a humidity, a volume, and an airflow of an inspection target in the body and may utilize the measured data for diagnosing a disease of the inspection target, when performing endoscopy.

Embodiments also provide a diagnosis assisting endoscope system and a controlling method of the diagnosis assisting endoscope system that may diagnose suspected diseases of an inspection target based on an image, a temperature, a humidity, a volume, and an airflow of the inspection target and may provide the diagnosed suspected diseases to an outside in real time, when performing endoscopy.

SOLUTIONS

According to an embodiment, there is provided a diagnosis assisting endoscope system including an endoscope module configured to insert into a body, and to sense an image, a temperature, a humidity, a volume, and an airflow of the body; an endoscope adaptor module connected to the endoscope module to receive sensing values of the endoscope module and to measure body sensing data; a central processing module connected in a signal transferable form to the endoscope adaptor module to store the body sensing data of the endoscope adaptor module as a setting type; and an auxiliary diagnosis module provided to at least one of the endoscope adaptor module and the central processing module, and configured to diagnose suspected diseases of the body in real time based on the body sensing data.

Since the diagnosis assisting endoscope system is used to diagnose the suspected diseases of the body by measuring the temperature, the humidity, the volume, and the airflow in addition to the image of the body, the diagnostic accuracy of endoscopy may be further enhanced.

According to an aspect, the diagnosis assisting endoscope system may further include a wireless communication module provided to the endoscope adaptor module and the central processing module to transfer a signal in a wireless manner between the endoscope adaptor module and the central processing module.

According to an aspect, the auxiliary diagnosis module may be configured to generate a disease diagnosis list about the suspected diseases of the body in real time, and the endoscope adaptor module may be configured to receive the disease diagnosis list and to output the received disease diagnosis list to an outside in real time. Accordingly, the diagnosis assisting endoscope system may utilize the disease diagnosis list for diagnosing the disease in real time while performing endoscopy in the body and accordingly, an endoscopic diagnosis may be quickly and conveniently performed.

According to an aspect, the endoscope module may include an endoscope body provided in a shape of which one end is inserted into the body, and configured to take an image of an inspection target of the body; a temperature sensor provided at a first portion of one end of the endoscope body to measure a temperature of the inspection target; a humidity sensor provided at a second portion of one end of the endoscope body to measure a humidity of the inspection target; an airflow sensor provided at a third portion of one end of the endoscope body to measure an airflow of the inspection target; and a volume sensor provided at a fourth portion of one end of the endoscope body to measure a volume of the inspection target. The endoscope adaptor module may include an image processing unit connected at another end of the endoscope body, and configured to generate image data in the body sensing data based on image information acquired by the endoscope body; a sensor processing unit connected in a signal transferable form to the temperature sensor, the humidity sensor, the airflow sensor, and the volume sensor, and configured to measure temperature data, humidity data, airflow data, and volume data in the body sensing data based on sensing values of the temperature sensor, the humidity sensor, the airflow sensor, and the volume sensor; and a display unit connected to the auxiliary diagnosis module, and configured to display the disease diagnosis list about the suspected diseases of the body generated by the auxiliary diagnosis module in real time.

Alternatively, the endoscope module may include an endoscope body provided in a shape of which one end is inserted into the body, and configured to take an image of an inspection target of the body; a temperature sensor provided at a first portion of one end of the endoscope body to measure a temperature of the inspection target; a humidity sensor provided at a second portion of one end of the endoscope body to measure a humidity of the inspection target; and an airflow sensor provided at a third portion of one end of the endoscope body to measure an airflow of the inspection target. The endoscope adaptor module may include an image processing unit connected at another end of the endoscope body, and configured to generate image data and volume data in the body sensing data based on image information acquired by the endoscope body; a sensor processing unit connected in a signal transferable form to the temperature sensor, the humidity sensor, and the airflow sensor, and configured to measure temperature data, humidity data, and airflow data in the body sensing data based on sensing values of the temperature sensor, the humidity sensor, and the airflow sensor; and a display unit connected to the auxiliary diagnosis module and configured to display the disease diagnosis list about the suspected diseases of the body generated by the auxiliary diagnosis module in real time.

According to an aspect, the central processing module may include a data conversion unit connected in a signal transferable form to the endoscope adaptor module, and configured to convert the body sensing data to the setting type; and a data storage unit connected to the data conversion unit, and configured to store the body sensing data converted by the data conversion unit.

The auxiliary diagnosis module may include a learning data storage unit configured to store disease learning data including feature information of diseases as the setting type; and a disease diagnosis unit connected in a signal transferable form to the learning data storage unit and the data storage unit, and configured to diagnose the suspected diseases of the body by comparing the body sensing data and the disease learning data.

Here, the auxiliary diagnosis module may be provided only to the central processing module. In this instance, the central processing module may be configured to transfer, to the endoscope adaptor module, the disease diagnosis list about the suspected diseases of the body generated by the auxiliary diagnosis module, and the endoscope adaptor module may be configured to display the disease diagnosis list to an outside in real time.

Alternatively, the auxiliary diagnosis module may be provided only to the endoscope adaptor module. In this instance, the central processing module may be configured to provide the body sensing data of the data storage unit to the auxiliary diagnosis module, and the endoscope adaptor module may be configured to display the disease diagnosis list about the suspected diseases of the body generated by the auxiliary diagnosis module to an outside in real time.

Alternatively, the auxiliary diagnosis module may include a first auxiliary diagnosis module provided to the central processing module and a second auxiliary diagnosis module provided to the endoscope adaptor module. In this instance, a first disease diagnosis unit of the first auxiliary diagnosis module may be configured to generate a first disease diagnosis list about the suspected diseases of the body based on the body sensing data stored in the data storage unit and the disease learning data stored in a first learning data storage unit. A second disease diagnosis unit of the second auxiliary diagnosis module may be configured to generate a second disease diagnosis list about the suspected diseases of the body based on the body sensing data stored in the data storage unit and the disease learning data of a second learning data storage unit that shares data of the first learning data storage unit.

The endoscope adaptor module may be configured to display the second disease diagnosis list to an outside in real time. The central processing module may further include a control unit configured to correct and supplement the second disease diagnosis list displayed by the endoscope adaptor module by comparing the first disease diagnosis list and the second disease diagnosis list.

According to another embodiment, there is provided a controlling method of a diagnosis assisting endoscope system, the method including sensing an image, a temperature, a humidity, a volume, and an airflow of a body in real time; measuring body sensing data including image data, temperature data, humidity data, volume data, and airflow data based on sensing values of the image, the temperature, the humidity, the volume, and the airflow of the body; changing a type of the body sensing data to be the same setting type as disease learning data that includes feature information of diseases; diagnosing suspected diseases of the body by comparing the body sensing data and the disease learning data; generating a disease diagnosis list about the suspected diseases of the body; and outputting the disease diagnosis list to an outside in real time.

According to an aspect, the controlling method of the diagnosis assisting endoscope system may further include constructing the disease learning data prior to comparing the body sensing data and the disease learning data.

Here, the constructing of the disease learning data may include collecting information about the diseases; extracting feature information of the diseases by learning information about the diseases; modeling a boundary value or a shape of feature learning information of the diseases by analyzing the feature learning information; converting the modeled feature learning information to disease learning data of the setting type; and storing the disease learning data.

The constructing of the disease learning data may further include transmitting the stored disease learning data to the diagnosis assisting endoscope system; and updating the diagnosis assisting endoscope system with the disease learning data.

Also, the comparing of the body sensing data and the disease learning data may include determining a position of a measurement value of the body sensing data based on a boundary value of the disease learning data or determining a similarity level between the body sensing data and a shape of the disease learning data.

EFFECTS

A diagnosis assisting endoscope system and a controlling method of the diagnosis assisting endoscope system according to embodiments may measure an image, a temperature, a humidity, a volume, and an airflow of an inspection target in the body and may utilize the measured data for diagnosing a disease of the inspection target. Accordingly, it is possible to further enhance the diagnostic accuracy of endoscopy and to prevent the occurrence of medical malpractice by an inaccurate diagnosis.

Also, a diagnosis assisting endoscope system and a controlling method of the diagnosis assisting endoscope system according to embodiments may diagnose suspected diseases of an inspection target based on body sensing data including an image, a temperature, a humidity, a volume, and an airflow of the inspection target, and may provide the diagnosed suspected diseases to an outside in real time and thus, may perform endoscopy while verifying the disease diagnosis list in real time. Accordingly, it is possible to quickly and accurately diagnose a disease of the body and to decrease an amount of clinic time used for endoscopy.

Also, a diagnosis assisting endoscope system and a controlling method of the diagnosis assisting endoscope system according to embodiments may generate a disease diagnosis list based on objective data such as body sensing data and disease learning data. Accordingly, when performing endoscopy, it is possible to secure the objectiveness of diagnosis about an inspection target of the body and to decrease a probability of malpractice that may occur due to negligence and a mistake of a doctor.

Also, a diagnosis assisting endoscope system and a controlling method of the diagnosis assisting endoscope system according to embodiments may conveniently update disease learning data even after constructing the disease learning data that includes feature information about various types of diseases, such as an image, a temperature, a humidity, a volume, and an airflow. Accordingly, it is possible to quickly cope with a new disease and to enhance the diagnostic accuracy by increasing the accuracy of disease learning data.

MODE FOR CARRYING OUT THE INVENTION

Figure 1:
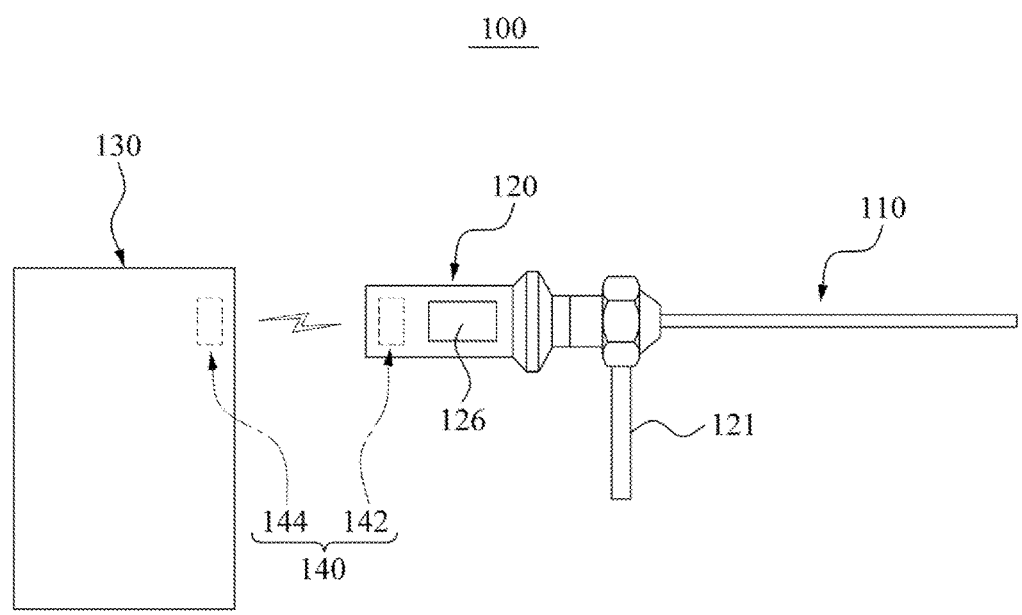
FIG. 1 illustrates a diagnosis assisting endoscope system according to an embodiment.

Hereinafter, example embodiments will be described with reference to the accompanying drawings. However, the present disclosure is not limited thereto or restricted thereby. Like reference numerals illustrated in the drawings refer to like elements throughout.

Figure 2:
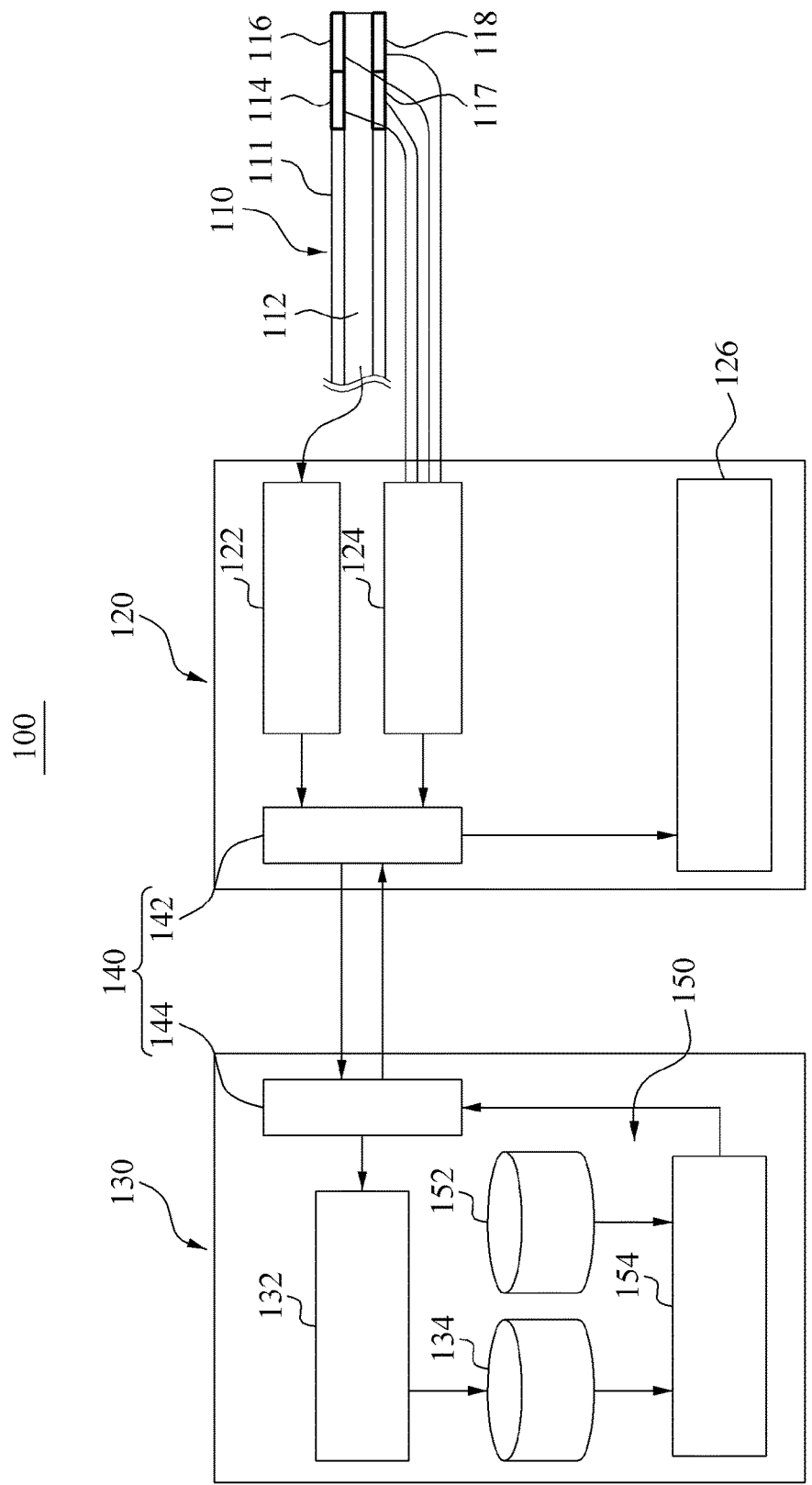
FIG. 2 illustrates a configuration of the diagnosis assisting endoscope system of FIG. 1

FIG. 1 illustrates a diagnosis assisting endoscope system 100 according to an embodiment, and FIG. 2 illustrates a configuration of the diagnosis assisting endoscope system 100 of FIG. 1.

Referring to FIGS. 1 and 2, the diagnosis assisting endoscope system 100 according to an embodiment includes an endoscope module 110, an endoscope adaptor module 120, a central processing module 130, a wireless communication module 140, and an auxiliary diagnosis module 150.

The endoscope module 110 is a device that is inserted into the body of a subject to have endoscopy and senses a state of the body in real time. The endoscope module 110 may be provided in a bar structure to be readily inserted into the body and, if necessary, may be provided in a bendable structure. Hereinafter, for clarity of description, the diagnosis assisting endoscope system 100 will be described based on an endoscope system for otolaryngology as an example. The endoscope system for otolaryngology may be inserted into a throat, an ear, or a nose, and may verify an internal state of the throat, the ear, or the nose.

The endoscope module 110 may be configured to simultaneously sense an image, a temperature, a humidity, a volume, and an airflow of the body. In particular, in the case of otolaryngology diseases, information about the temperature, the humidity, the volume, and the airflow of the body may be utilized as very important criteria to diagnose otolaryngology diseases. For example, the endoscope module 110 may include an endoscope body 112, a temperature sensor 114, a humidity sensor 116, a volume sensor 117, and an airflow sensor 118.

Here, the endoscope body 112 is a device that takes an image of an inspection target in the body in real time. The endoscope body 112 may be provided in a bar shape of which a cross-section has a relatively small radius, so that one end of the endoscope body 112 may be readily inserted in the throat, the ear, or the nose. Meanwhile, the endoscope body 112 may be embedded with a light source and a camera to be capable of directly taking an image of the body. Alternatively, the endoscope body 112 may be configured to transfer light of the light source and the image of the body so that the light source and the camera provided at an outside may take the image of the body.

Hereinafter, the present embodiment will be described based on an example in which the light source (not shown) and the camera (not shown) are provided to the endoscope adaptor module 120 and are connected at another end of the endoscope body 112. For example, a protruding portion 121 may be protruded from a portion of the endoscope adaptor module 120 that is connected at the other end of the endoscope body 112. The light source and the camera may be provided to the protruding portion 121. The protruding portion 121 may be protruded in a pipeline shape from the endoscope adaptor module 120 in a direction orthogonal to the endoscope body 112. The light source and the camera may be provided in the protruding portion 121 in an embedded structure, or may be mounted to the protruding portion 121 in a replaceable structure.

The temperature sensor 114 is a device that measures a temperature of the inspection target of the body in real time, and the humidity sensor 116 is a device that measures a humidity of the inspection target of the body in real time. Also, the volume sensor 117 is a device that measures a volume of the inspection target of the body in real time, and the airflow sensor 118 is a device that measures an airflow of the inspection target of the body.

Referring to FIG. 2, the temperature sensor 114, the humidity sensor 116, the volume sensor 117, and the airflow sensor 118 may be provided in a singular form on different portions of one end of the endoscope body 112, respectively. However, it is only an example and the number to be installed and the arrangement structure for the temperature sensor 114, the humidity sensor 116, the volume sensor 117, and the airflow sensor 118 may be variously modified based on a design condition and a situation of the diagnosis assisting endoscope system 100. That is, a plurality of temperature sensors 114, humidity sensors 116, volume sensors 117, and airflow sensors 118 may be installed on one end of the endoscope body 112. Further, the temperature sensor 114, the humidity sensor 116, the volume sensor 117, and the airflow sensor 118 may be spaced apart from each other along the periphery of one end of the endoscope body 112, or may be mounted to be separate from each other in a lengthwise direction at one end of the endoscope body 112.

For example, the temperature sensor 114 may be mounted to each of an upper portion and a lower portion of one end of the endoscope body 112. In this case, temperatures of an upper portion and a lower portion of the inspection target into which one end of the endoscope body 112 is to be inserted may be simultaneously measured. Alternatively, the temperature sensor 114 may be mounted to each of the upper portion, the lower portion, a left portion, and a right portion of one end of the endoscope body 112. In this case, temperatures of the upper portion, the lower portion, the left portion, and the right portion of the inspection target into which one end of the endoscope body 112 is to be inserted may be simultaneously measured. As described above, when the plurality of temperature sensors 114 is disposed at different positions, respectively, the temperature distribution around the inspection target of the body may be further accurately measured.

Similar to the temperature sensor 114, a plurality of humidity sensors 116, volume sensors 117, or airflow sensors 118 may be disposed at different positions, respectively. Accordingly, the humidity, the volume, or the airflow may be measured in every direction of the inspection target of the body.

Each of the temperature sensor 114, the humidity sensor 116, the volume sensor 117, and the airflow sensor 118 may be configured as a thin film flexible sensor to barely increase the radius of the endoscope body 112. Accordingly, it is possible to prevent an enlargement of the endoscope module 110 that may occur due to the installation of the temperature sensor 114, the humidity sensor 116, the volume sensor 117, and the airflow sensor 118.

Referring to FIG. 1 or FIG. 2, the endoscope adaptor module 120 is a device that receives sensing values of the endoscope module 110 and measures body sensing data. The body sensing data may include image data, temperature data, humidity data, volume data, and airflow data about the inspection target of the body.

Here, the endoscope adaptor module 120 may be connected in a signal transferable form to the endoscope module 110. That is, the endoscope adaptor module 120 may be detachably coupled with the endoscope module 110. For example, the endoscope adaptor module 120 may include an image processing unit 122, a sensor processing unit 124, and a display unit 126.

The image processing unit 122 is a device that generates image data in body sensing data based on image information acquired by the endoscope body 112. The image processing unit 122 may be directly connected at the other end of the endoscope body 112. The image processing unit 122 may include the light source and the camera. That is, light generated from the light source of the image processing unit 122 may be transferred to an inside of the body through the endoscope body 112. Real-time image information transferred through the endoscope body 112 may be transferred to the camera of the image processing unit 122.

The sensor processing unit 124 is a device that measures temperature data, humidity data, volume data, and airflow data in body sensing data based on sensing values of the temperature sensor 114, the humidity sensor 116, the volume sensor 117, and the airflow sensor 118. The sensor processing unit 124 may be connected in a signal transferable form to the temperature sensor 114, the humidity sensor 116, the volume sensor 117, and the airflow sensor 118. Hereinafter, the present embodiment will be described based on an example in which the sensor processing unit 124 is connected to the temperature sensor 114, the humidity sensor 116, the volume sensor 117, and the airflow sensor 118 through cables. However, it is only an example and a variety of signal transfer methods may be applied for the connections.

Alternatively, the image processing unit 122 may generate image data and volume data in body sensing data based on image data acquired by the endoscope body 112. For example, the image processing unit 122 may generate image data based on the image information and may extract volume data of the inspection target by analyzing the image data. In this case, the endoscope module 110 may include only the temperature sensor 114, the humidity sensor 116, and the airflow sensor 118. The sensor processing unit 124 may measure only temperature data, humidity data, and airflow data in body sensing data.

Alternatively, the endoscope module 110 may include at least one of the temperature sensor 114, the humidity sensor 116, the volume sensor 117, and the airflow sensor 118. In this case, the sensor processing unit 124 may measure only at least one of temperature data, humidity data, volume data, and airflow data in body sensing data, and the auxiliary diagnosis module 150 may diagnose suspected diseases of the body using only the measured data.

Hereinafter, the present embodiment will be described based on an example in which the endoscope module 110 includes the temperature sensor 114, the humidity sensor 116, the volume sensor 117, and the airflow sensor 118, and the sensor processing unit 124 receives sensing values of the temperature sensor 114, the humidity sensor 116, the volume sensor 117, and the airflow sensor 118 and measures temperature data, humidity data, volume data, and airflow data.

The display unit 126 is a device that indicates a disease diagnosis list about the suspected diseases of the body generated by the auxiliary diagnosis module 150. The display unit 126 may be connected to the auxiliary diagnosis module 150 to be capable of receiving the disease diagnosis list. For example, the display unit 126 may be provided as a display device, for example, a light emitting diode (LED) or a liquid crystal display (LCD), to visually display the disease diagnosis list.

Referring to FIG. 1 or FIG. 2, the central processing module 130 is a device that stores body sensing data of the endoscope adaptor module 120 as a setting type. The central processing module 130 may be connected in a signal transferrable form to the endoscope adaptor module 120. For example, the central processing module 130 may include a data conversion unit 132 and a data storage unit 134.

The data conversion unit 132 is a device that converts the body sensing data to the setting type. That is, in the case of the body sensing data of the endoscope adaptor module 120, a data structure may be changed to be the same type as disease learning data by the data conversion unit 132. The disease learning data will be described later. Accordingly, a comparison between the body sensing data and the disease learning data may be readily and quickly performed. In addition, data may be very efficiently stored and managed. The data conversion unit 132 may be connected in a signal transferable form to the endoscope adaptor module 120 to receive the body sensing data from the endoscope adaptor module 120 in real time.

The data storage unit 134 is a device that stores body sensing data converted by the data conversion unit 132. That is, the body sensing data may be stored in the data storage unit 134 in a state in which a type of the body sensing data is changed to be the setting type by the data conversion unit 132. The body sensing data may be stored and managed in the data storage unit 134 based on a file or a database management system (DBMS). The data conversion unit 132 may be connected in a signal transferable form to the data conversion unit 132.

Referring to FIGS. 1 and 2, the wireless communication module 140 is a device that transfers a signal between the endoscope adaptor module 120 and the central processing module 130. The wireless communication module 140 may be provided to the endoscope adaptor module 120 and the central processing module 130 to bi-directionally transmit a variety of signals and data in a wireless manner. For example, the wireless communication module 140 may be configured using a variety of wireless communication methods, for example, wireless fidelity (Wi-Fi), Bluetooth, and ultra wideband (UWB).

The wireless communication module 140 may include a first wireless communication unit 142 provided to the endoscope adaptor module 120 and a second wireless communication unit 144 provided to the central processing module 130. The first wireless communication unit 142 and the second wireless communication unit 144 may be configured to transfer various types of data and signals mutually and bi-directionally.

The first wireless communication unit 142 and the second wireless communication unit 144 may be configured to communicate with each other in a one-to-one manner, or may be configured to communicate with each other in a one-to-many manner or a many-to-many manner. Hereinafter, the present embodiment will be described based on an example in which the plurality of first wireless communication units 142 is simultaneously connected to a single second wireless communication unit 144.

Referring to FIGS. 1 and 2, the auxiliary diagnosis module 150 is a device that diagnoses the suspected diseases of the body in real time based on body sensing data. The auxiliary diagnosis module 150 may be provided to at least one of the endoscope adaptor module 120 and the central processing module 130. Hereinafter, the present embodiment will be described based on an example in which the auxiliary diagnosis module 150 is provided only to the central processing module 130. Other embodiments will be described later.

The auxiliary diagnosis module 150 may generate a disease diagnosis list about the suspected diseases of the body in real time. The disease diagnosis list refers to a candidate set of suspected diseases that are determined based on body sensing data when performing endoscopy, and may be displayed to an outside in real time using the display unit 126 of the endoscope adaptor module 120. Accordingly, since the disease diagnosis list is displayed on the display unit 126 in real time during endoscopy of otolaryngology, the diagnosis assisting endoscope system according to an embodiment enables a doctor to quickly and accurately make a diagnosis by referring to the disease diagnosis list while performing endoscopy. For example, the auxiliary diagnosis module 150 may include a learning data storage unit 152 and a disease diagnosis unit 154.

Disease learning data that includes feature information of various diseases may be stored as the setting type in the learning data storage unit 152. The disease learning data refers to data in which feature information about various diseases is included as the setting type, and may be utilized to select suspected diseases of the body through comparison and analysis with body sensing data. That is, the disease learning data refers to data acquired by learning knowledge and experience of medical experts or a variety of disease information collected on the medical treatment field and by extracting and modeling feature learning information for each disease.

The disease learning data may be prepared in advance and may be stored in the learning data storage unit 152 in various forms. For example, features or critical areas of disease learning data may be stored in a form based on, for example, a rule, a pattern, a markup language in a type of extensible markup language (XML), or a DBMS table. In addition, the disease learning data may be stored in the learning data storage unit 152 at the time of manufacturing the diagnosis assisting endoscope system 100. Even after then, the disease learning data may be continuously updated.

The disease diagnosis unit 154 is a device that generates the disease diagnosis list about the suspected diseases of the body by comparing and analyzing the body sensing data and the disease learning data and by diagnosing the suspected diseases of the body. The disease diagnosis unit 154 may be connected in a signal transferable form to the learning data storage unit 152 and the data storage unit 134. That is, the disease diagnosis unit 154 may receive body sensing data sensed in real time through the data storage unit 134, and may receive disease learning data about various types of diseases through the learning data storage unit 152. Accordingly, the disease diagnosis unit 154 may select disease learning data including body sensing data by performing comparison and analysis on the disease learning data and the body sensing data, and may verify diseases corresponding to the selected disease learning data.

The generated disease diagnosis list may be transferred from the central processing module 130 to the endoscope adaptor module 120 through the wireless communication module 140, and may be displayed to an outside through the display unit 126 of the endoscope adaptor module 120. Accordingly, the diagnosis assisting endoscope system 100 may accurately diagnose the suspected diseases of the body based on the image, the temperature, the humidity, the volume, and the airflow of the body, and may assist a diagnosis of endoscopy by displaying the disease diagnosis list about the suspected diseases of the body in real time.

Figure 3:
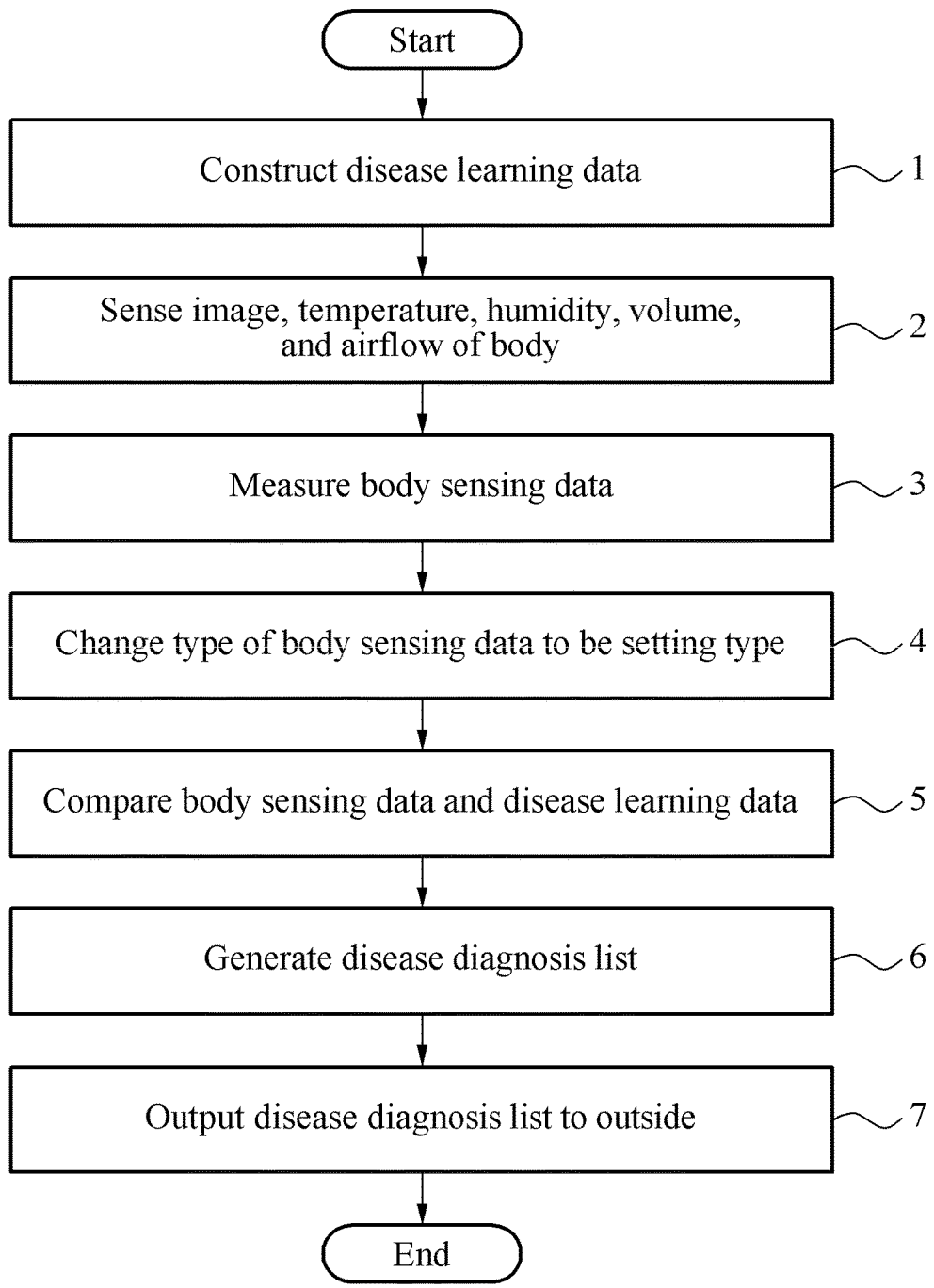
FIG. 3 is a flowchart illustrating a controlling method of a diagnosis assisting endoscope system according to an embodiment.
Figure 4:
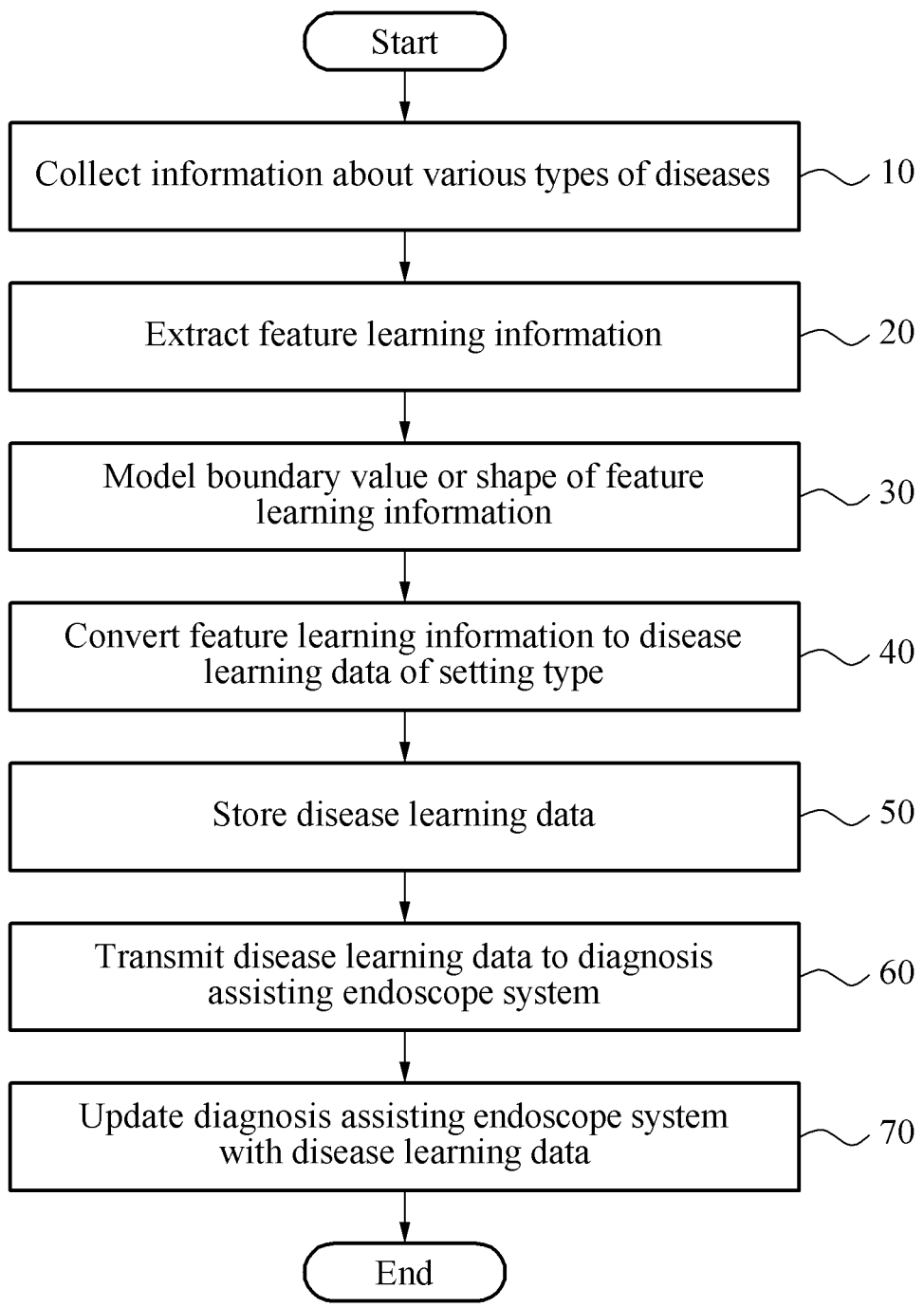
FIG. 4 is a flowchart illustrating an operation of constructing disease learning data of FIG. 3.

Hereinafter, a controlling method of the diagnosis assisting endoscope system 100 constructed as above will be described. FIG. 3 is a flowchart illustrating a controlling method of the diagnosis assisting endoscope system 100 according to an embodiment, and FIG. 4 is a flowchart illustrating an operation of constructing disease learning data of FIG. 3.

Referring to FIG. 3, the controlling method of the diagnosis assisting endoscope system 100 includes operation 2 of sensing an image, a temperature, a humidity, a volume, and an airflow of a body in real time, operation 3 of measuring body sensing data that includes image data, temperature data, humidity data, volume data, and airflow data, based on sensing values of the image, the temperature, the humidity, the volume, and the airflow of the body, operation 4 of changing a type of the body sensing data to be the same type as disease learning data that includes feature information about various types of diseases, operation 5 of diagnosing suspected diseases of the body by comparing the body sensing data and the disease learning data, operation 6 of generating a disease diagnosis list about the suspected diseases of the body, and operation 7 of outputting the disease diagnosis list to an outside in real time.

In operation 2 of sensing the image, the temperature, the humidity, the volume, and the airflow of the body, one end of the endoscope module 110 may be inserted into the body and may sense an image, a temperature, a humidity, a volume, and an airflow of an inspection target of the body. For example, the endoscope body 112, the temperature sensor 114, the humidity sensor 116, the volume sensor 117, and the airflow sensor 118 of the endoscope module 110 may sense the image, the temperature, the humidity, the volume, and the airflow of the inspection target.

In operation 3 of measuring body sensing data, the endoscope adaptor module 120 may receive sensing values of the endoscope module 110, and may measure image data, temperature data, humidity data, volume data, and airflow data. For example, the image processing unit 122 of the endoscope adaptor module 120 may measure image data by receiving image information of the endoscope body 112. The sensor processing unit 124 of the endoscope adaptor module 120 may measure temperature data, humidity data, volume data, and airflow data by receiving sensing values of the temperature sensor 114, the humidity sensor 116, the volume sensor 117, and the airflow sensor 118.

In operation 4 of changing a type of body sensing data to be the setting type, the wireless communication module 140 may wirelessly transmit body sensing data of the endoscope adaptor module 120 to the central processing module 130. The data conversion unit 132 of the central processing module 130 may receive the body sensing data and may change a type of the received body sensing data to be the setting type. That is, the type of body sensing data may be changed to be the same setting type as disease learning data by the data conversion unit 132 so that the body sensing data may be readily compared and analyzed with the disease learning data. The converted body sensing data may be stored in the data storage unit 134 of the central processing module 130.

In operation 5 of comparing the body sensing data and the disease learning data, the auxiliary diagnosis module 150 may diagnose the suspected diseases of the body by comparing and analyzing the body sensing data and the disease learning data. That is, the disease diagnosis unit 154 of the auxiliary diagnosis module 150 may diagnose the suspected diseases of the body by comparing and analyzing the body sensing data of the data storage unit 134 and the disease learning data of the learning data storage unit 152.

The disease learning data is acquired by modeling feature shapes and critical areas of image data, temperature data, humidity data, volume data, and airflow data for each disease. Accordingly, in operation 5 of comparing the body sensing data and the disease learning data, a position of a measurement value of body sensing data may be determined based on a boundary value of the disease learning data. Alternatively, a similarity level between a feature shape of the body sensing data and a shape of the disease learning data may be determined.

For example, it is possible to select disease learning data that includes a feature shape similar to image data of body sensing data and also includes temperature data, humidity data, volume data, and airflow data of body sensing data in a critical area. Further, it is possible to predict a disease corresponding to the selected disease learning data.

In operation 6 of generating a disease diagnosis list, a disease diagnosis list including suspected diseases diagnosed by the disease diagnosis unit 154 may be generated. The generated disease diagnosis list may be provided using a variety of arrangement methods. For example, the disease diagnosis list may be generated by sequentially listing suspected diseases of the body based on a mutual similarity level between body sensing data and disease learning data. Alternatively, the disease diagnosis list may be generated by sequentially listing suspected diseases of the body based on a correlation between diseases.

In operation 7 of outputting the disease diagnosis list to an outside in real time, the disease diagnosis list generated by the disease diagnosis unit 154 may be displayed to an outside in real time through the display unit 126 of the endoscope adaptor module 120. In detail, the disease diagnosis list of the disease diagnosis unit 154 may be transmitted from the central processing module 130 to the endoscope adaptor module 120 through the wireless communication module 140 and then be displayed on the display unit 126 of the endoscope adaptor module 120. Accordingly, when performing endoscopy, an otolaryngologist may diagnose otolaryngology diseases while verifying the disease diagnosis list displayed on the display unit 126 in real time.

Referring to FIGS. 3 and 4, the controlling method of the diagnosis assisting endoscope system 100 according to an embodiment may further include operation 1 of constructing the disease learning data prior to operation 5 of comparing the body sensing data and the disease learning data. Hereinafter, the present embodiment will be described based on an example in which operation 1 of constructing the disease learning data is performed prior to operation 2 of sensing the image, the temperature, the humidity, the volume, and the airflow of the body.

For example, operation 1 of constructing the disease learning data may include operation 10 of collecting information about various types of diseases, operation 20 of extracting feature information about a disease by learning information about the various types of diseases, operation 30 of modeling a boundary value or a shape of feature learning information of a disease by analyzing feature learning information, operation 40 of converting the modeled feature learning information to disease learning data of the setting type, and operation 50 of storing the disease learning data.

In operation 10 of collecting information about various types of diseases, professional knowledge about the existing various types of diseases may be collected from an expert group of a corresponding disease and experience and information may be collected on the medical treatment field in real time.

In operation 20 of extracting feature information, feature information about the various types of diseases may be extracted by learning information about the various types of diseases collected in operation 10. That is, related experts may select and confirm feature learning information capable of defining or identifying a specific disease by learning information about various types of diseases.

In operation 30 of modeling a boundary value or a shape of feature learning information, the feature learning information confirmed in operation 20 may be analyzed and a boundary value or a feature shape of the feature learning information may be modeled. The modeled boundary value or feature shape may be utilized as a criterion to determine various types of diseases.

In operation 40 of converting feature learning information to disease learning data, disease learning data may be obtained by converting the feature learning information modeled in operation 30 to data of the setting type. Accordingly, the disease learning data includes contents, for example, a boundary value of a critical range and a feature shape of the feature learning information, about the disease.

In operation 50 of storing the disease learning data, a disease learning data database may be generated by systematically storing the disease learning data of which a type is changed to the setting type in operation 40.

Hereinafter, a process of constructing disease learning data will be further described.

In disease learning data, image data is stored by collecting an image of a specific disease, by extracting, from the image, a region of interest (ROI) capable of specifying the disease, by recognizing a feature shape, for example, a contour shape, a color, and a surface shape, of the ROI by modeling the feature shape, and by generating, as data, modeling information of the feature shape in a form of a table based on, for example, a rule, a pattern, a markup language in a type of XML, or a DBMS. Meanwhile, in operation 4 of changing a type of body sensing data to be the setting type, image data of body sensing data may be extracted from image information of the inspection target of the body and stored in the same manner as the process of constructing image data of disease learning data.

In disease learning data, temperature data, humidity data, volume data, and airflow data are stored by collecting information about a temperature, a humidity, a volume, and an airflow of the specific disease, by extracting a critical area and acceleration capable of specifying the disease, by modeling a boundary value of the critical area and the acceleration, and by generating, as data, the modeled boundary value in a form of a table based on, for example, a rule, a pattern, a markup language in a type of XML, or a DBMS. Meanwhile, in operation 4 of changing a type of body sensing data to be the setting type, temperature data, humidity data, volume data, and airflow data of body sensing data may be extracted from measurement values of the temperature, the humidity, the volume, and the airflow of the inspection target of the body and stored in the same manner as the process of constructing temperature data, humidity data, volume data, and airflow data of disease learning data.

Operation 1 of constructing disease learning data according to the present embodiment may further include operation 60 of transmitting the disease learning data to the diagnosis assisting endoscope system 100 and operation 70 of updating the diagnosis assisting endoscope system 100 with the disease learning data. That is, in operation 1 of constructing the disease learning data, the disease learning data of the diagnosis assisting endoscope system 100 may be continuously updated by transmitting the newly constructed disease learning data to the diagnosis assisting endoscope system 100. Accordingly, the diagnosis assisting endoscope system 100 may continuously enhance the disease diagnosis performance.

Figure 5:
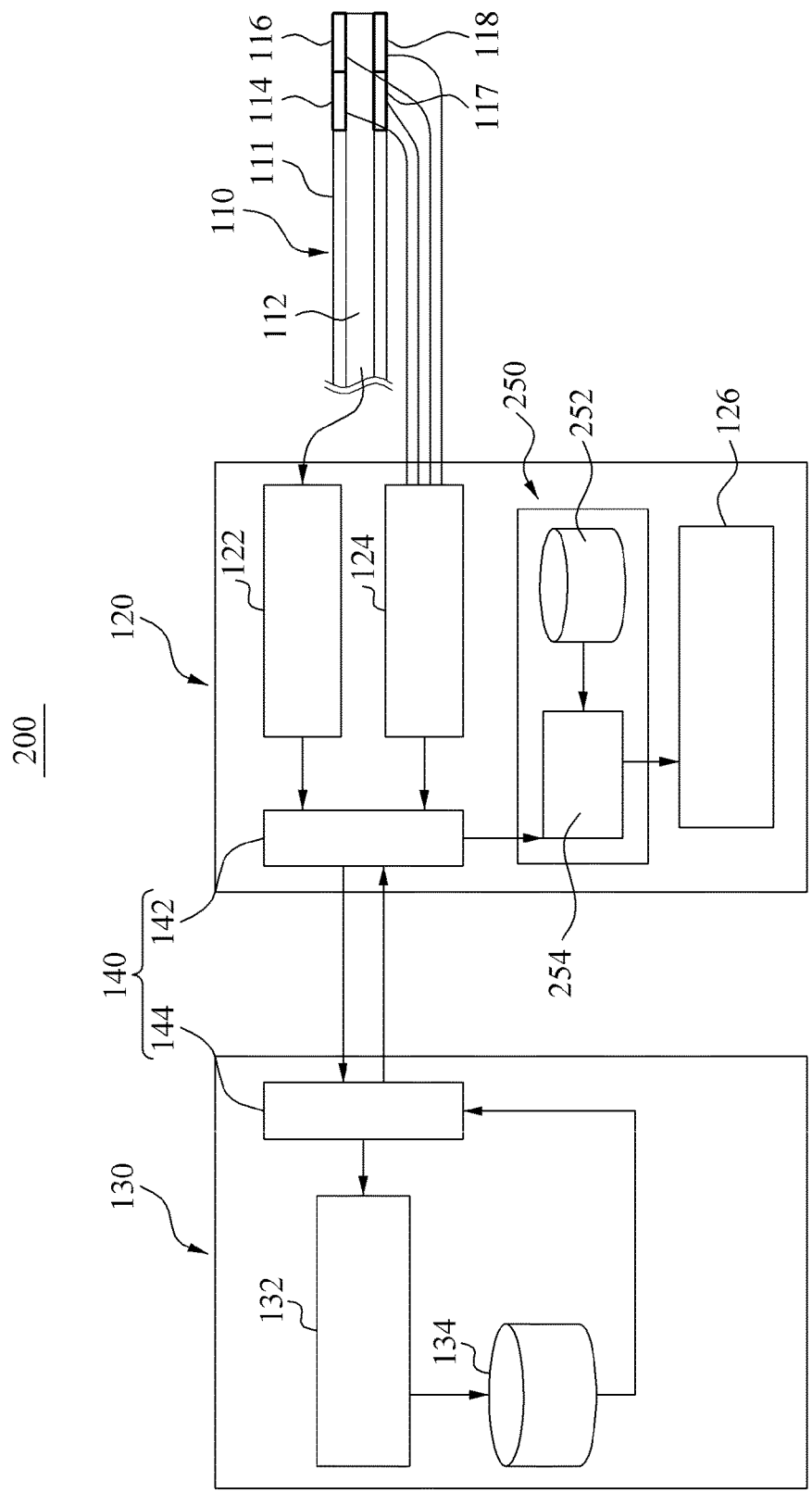
FIG. 5 illustrates a configuration of a diagnosis assisting endoscope system according to another embodiment.

FIG. 5 illustrates a configuration of a diagnosis assisting endoscope system 200 according to another embodiment.

Figure 6:
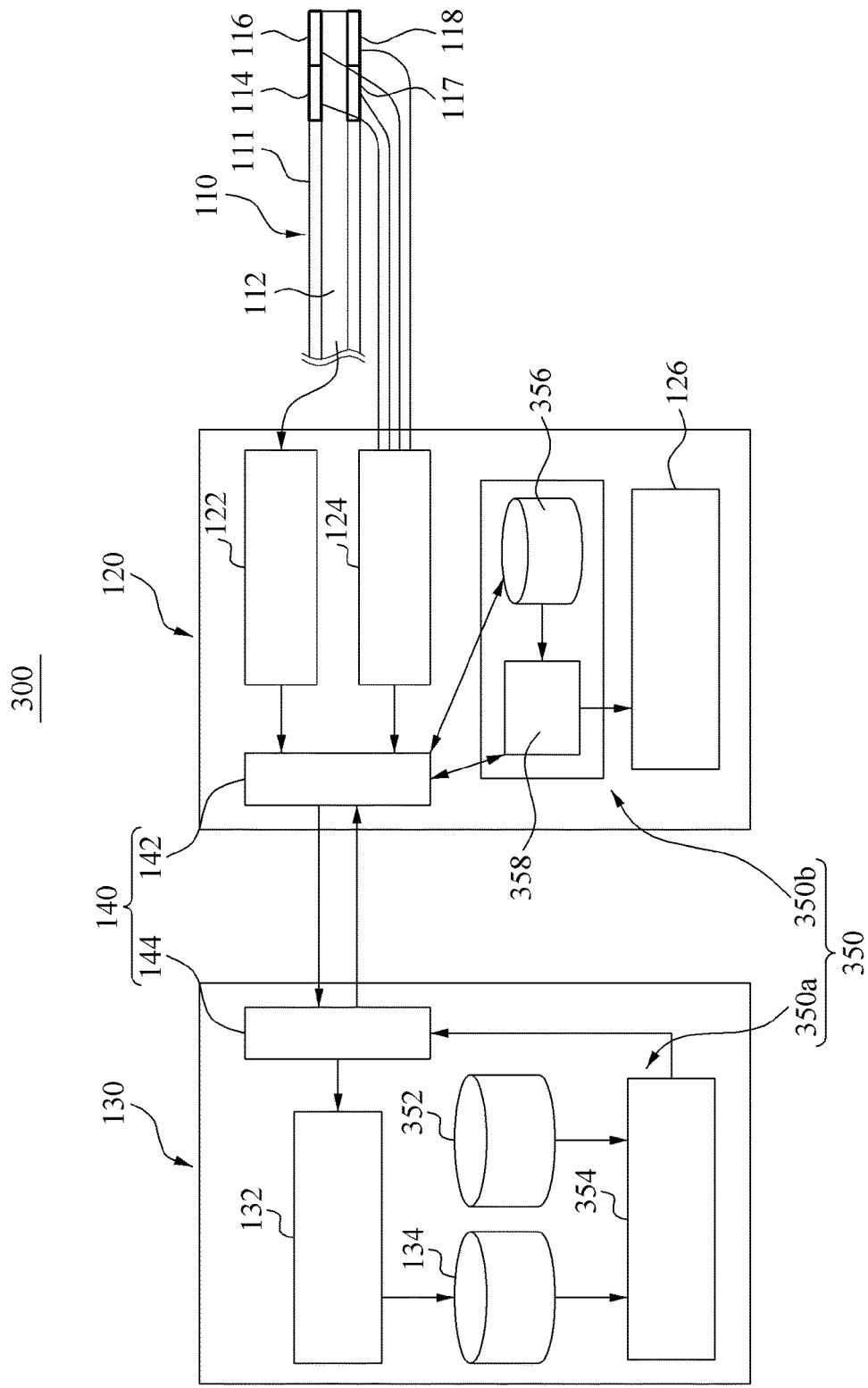
FIG. 6 illustrates a configuration of a diagnosis assisting endoscope system according to still another embodiment.

Reference numerals of FIG. 6 the same as or similar to reference numerals of FIGS. 1 and 2 refer to the like constituent elements and thus, a further description related thereto will be omitted here. Hereinafter, a description will be made based on a difference between the diagnosis assisting endoscope system 200 of FIG. 5 and the diagnosis assisting endoscope system 100 of FIGS. 1 and 2.

Referring to FIG. 5, the diagnosis assisting endoscope system 200 according to another embodiment differs from the diagnosis assisting endoscope system 100 of FIGS. 1 and 2 only in that an auxiliary diagnosis module 250 is provided only to the endoscope adaptor module 120.

For example, the auxiliary diagnosis module 250 may be embedded in the endoscope adaptor module 120, may be connected in a signal transferable form to the endoscope adaptor module 120 by a data cable, or may be provided to the endoscope adaptor module 120 in a docking structure. Hereinafter, the present embodiment will be described based on an example in which the auxiliary diagnosis module 250 is embedded in the endoscope adaptor module 120.

The auxiliary diagnosis module 250 may include a learning data storage unit 252 and a disease diagnosis unit 254. The learning data storage unit 252 and the disease diagnosis unit 254 may perform the same functionalities as the learning data storage unit 152 and the disease diagnosis unit 154 of FIG. 2 and thus, a further description related thereto will be omitted. The auxiliary diagnosis module 250 may be configured as an embedded system and may be configured based on a smartphone platform, for example, Android and Windows.

Here, the central processing module 130 may provide body sensing data of the data storage unit 134 to the disease diagnosis unit 254 of the auxiliary diagnosis module 250 through the wireless communication module 140. For example, the central processing module 130 may directly transfer body sensing data to the disease diagnosis unit 254 through the wireless communication module 140. Alternatively, the central processing module 130 may transmit the body sensing data to the endoscope adaptor module 120 through the wireless communication module 140 and the endoscope adaptor module 120 may transfer the body sensing data to the disease diagnosis unit 254.

The endoscope adaptor module 120 may be configured to display a disease diagnosis list generated by the disease diagnosis unit 254 of the auxiliary diagnosis module 250 to an outside in real time. For example, the display unit 126 of the endoscope adaptor module 120 may be directly connected to the disease diagnosis unit 254 to directly receive the disease diagnosis list of the auxiliary diagnosis module 250.

FIG. 6 illustrates a configuration of a diagnosis assisting endoscope system 300 according to still another embodiment.

Reference numerals of FIG. 6 the same as or similar to reference numerals of FIGS. 1 and 2 refer to the like constituent elements and thus, a further description related thereto will be omitted here. Hereinafter, a description will be made based on a difference between the diagnosis assisting endoscope system 300 of FIG. 6 and the diagnosis assisting endoscope system 100 of FIGS. 1 and 2.

Referring to FIG. 6, the diagnosis assisting endoscope system 300 according to still another embodiment differs from the diagnosis assisting endoscope system 100 of FIGS. 1 and 2 only in that an auxiliary diagnosis module 350 is provided to each of the endoscope adaptor module 120 and the central processing module 130.

For example, the auxiliary diagnosis module 350 may include a first auxiliary diagnosis module 350a provided to the central processing module 130 and a second auxiliary diagnosis module 350b provided to the endoscope adaptor module 120.

The first auxiliary diagnosis module 350a may include a first learning data storage unit 352 that stores disease learning data and a first disease diagnosis unit 354 connected in a signal transferable form to the first learning data storage unit 352 and the data storage unit 134 to compare body sensing data and the disease learning data of the first learning data storage unit 352 and to diagnose suspected diseases of the body. Here, the first auxiliary diagnosis module 350a may be provided in a configuration similar to a configuration of the auxiliary diagnosis module 150 of FIGS. 1 and 2. Accordingly, the first disease diagnosis unit 354 of the first auxiliary diagnosis module 350a may generate a first disease diagnosis list about the suspected diseases of the body based on the body sensing data stored in the data storage unit 134 and the disease learning data stored in the first learning data storage unit 352.

Here, the second auxiliary diagnosis module 350b may include a second learning data storage unit 356 that stores the disease learning data transferred from the first learning data storage unit 352 and a second disease diagnosis unit 358 connected in a signal transferable form to the second learning data storage unit and the data storage unit to compare the body sensing data and the disease learning data of the second learning data storage unit and to diagnose the suspected diseases of the body. Accordingly, the second disease diagnosis unit 358 of the second auxiliary diagnosis module 350b may generate a second disease diagnosis list about the suspected diseases of the body based on the body sensing data stored in the data storage unit 134 and the disease learning data of the second learning data storage unit 356 that shares data of the first learning data storage unit 352.

That is, the second auxiliary diagnosis module 350b may be configured to be overall similar to the auxiliary diagnosis module 250 of FIG. 5, however, differs in that the second learning data storage unit 356 receives and uses the disease learning data of the first learning data storage unit 352. For example, only disease learning data about a representatively frequently occurring disease may be selectively stored in the second learning data storage unit 356.

Accordingly, a storage capacity of the second learning data storage unit 356 may be less than a storage capacity of the first learning data storage unit 352. Since the second learning data storage unit 356 may be configured in a relatively small size compared to the first learning data storage unit 352, a miniaturization and a cost reduction of the second auxiliary diagnosis module 350b may be achieved. Also, the second auxiliary diagnosis module 350b diagnoses a disease based on the second learning data storage unit 356 having an amount of data less than the first learning data storage unit 352 and thus, may quickly diagnose the suspected diseases compared to a case of using the first auxiliary diagnosis module 350a. Accordingly, the disease diagnosis list may be quickly provided to an outside in real time.

Meanwhile, the display unit 126 of the endoscope adaptor module 120 may display one of the first disease diagnosis list and the second disease diagnosis list to an outside in real time. Hereinafter, the present embodiment will be described based on an example in which the second disease diagnosis list is displayed on the display unit 126 in real time.

Also, the central processing module 130 may further include a control unit (not shown) configured to correct and complement the second disease diagnosis list by comparing the first disease diagnosis list and the second disease diagnosis list. The control unit may receive and compare the first disease diagnosis list and the second disease diagnosis list. Also, the control unit may verify contents omitted or inaccurately represented in the second disease diagnosis list and may additionally display the verified contents to the outside again.

Referring to FIG. 6, when the first auxiliary diagnosis module 350a is provided to the endoscope adaptor module 120 and the second auxiliary diagnosis module 350b is provided to the central processing module 130, the second disease diagnosis list may be quickly provided to a user of the diagnosis assisting endoscope system 300 using the second auxiliary diagnosis module 350b. The first disease diagnosis list diagnosed in further detail may be provided using the first auxiliary diagnosis module 350a.

Also, the data conversion unit 132 of the central processing module 130 may be additionally provided to the inside of the endoscope adaptor module 120. Alternatively, a separate small device that functions as the data conversion unit 132 may be provided to be selectively connected to the endoscope adaptor module 120. In this case, endoscopy may be performed using only the endoscope module 110 and the endoscope adaptor module 120. Accordingly, endoscopy may be performed in a place in which wireless communication with the central processing module 130 is impossible.

Although a few embodiments have been shown and described, they are provided to help the general understanding of the present disclosure and the present disclosure is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A diagnosis assisting endoscope system comprising:
an endoscope configured to insert into a body, and to sense an image, a temperature, a humidity, a volume, and an airflow of the body;
an endoscope adaptor connected to the endoscope to receive sensing values of the endoscope and to measure body sensing data; and
a central processor connected in a signal transferable form to the endoscope adaptor module to store the body sensing data of the endoscope adaptor module as a setting type; and
wherein at least one of the central processor and the endoscope adaptor is configured to diagnose suspected diseases of the body in real time based on the body sensing data, and
wherein the central processor is configured to generate a disease diagnosis list about the suspected diseases of the body in real time, and the endoscope adaptor is configured to receive the disease diagnosis list and to output the received disease diagnosis list to an outside of the endoscope adaptor in real time,
wherein the central processor comprises:
a data converter connected in a signal transferable form to the endoscope adaptor, wherein the data converter is configured to convert the body sensing data to the setting type;
a data storage connected to the data converter, and configured to store the body sensing data converted by the data converter; and a learning data storage configured to store disease learning data comprising feature information of diseases as the setting type, wherein the central processor is configured to diagnose the suspected diseases of the body by comparing the body sensing data and the disease learning data, wherein the central processor is configured to generate a first disease diagnosis list about the suspected diseases of the body based on the body sensing data stored in the data storage and the disease learning data stored in a first learning data storage; and wherein the endoscope adaptor is configured to generate a second disease diagnosis list about the suspected diseases of the body based on the body sensing data stored in the data storage and the disease learning data of a second learning data storage that shares data of the first learning data storage.

2. The diagnosis assisting endoscope system of claim 1, further comprising:

a wireless communicator provided to the endoscope adaptor and the central processor to transfer a signal in a wireless manner between the endoscope adaptor and the central processor.

3. The diagnosis assisting endoscope system of claim 1, wherein the endoscope comprises:

an endoscope body provided in a shape of which one end is inserted into the body, and configured to take an image of an inspection target of the body;

a temperature sensor provided at a first portion of one end of the endoscope body to measure a temperature of the inspection target;

a humidity sensor provided at a second portion of one end of the endoscope body to measure a humidity of the inspection target;

an airflow sensor provided at a third portion of one end of the endoscope body to measure an airflow of the inspection target; and a volume sensor provided at a fourth portion of one end of the endoscope body to measure a volume of the inspection target.

4. The diagnosis assisting endoscope system of claim 3, wherein the endoscope adaptor comprises:

an image processor connected at another end of the endoscope body, and configured to generate image data in the body sensing data based on image information acquired by the endoscope body;

a sensor processor connected in a signal transferable form to the temperature sensor, the humidity sensor, the airflow sensor, and the volume sensor, and configured to measure temperature data, humidity data, airflow data, and volume data in the body sensing data based on sensing values of the temperature sensor, the humidity sensor, the airflow sensor, and the volume sensor; and a display connected in a signal transferable form to the central processor, and configured to display the disease diagnosis list about the suspected diseases of the body generated by the central processor in real time.

5. The diagnosis assisting endoscope system of claim 1, wherein the endoscope comprises:

an endoscope body provided in a shape of which one end is inserted into the body, and configured to take an image of an inspection target of the body;

a temperature sensor provided at a first portion of one end of the endoscope body to measure a temperature of the inspection target;

a humidity sensor provided at a second portion of one end of the endoscope body to measure a humidity of the inspection target; and an airflow sensor provided at a third portion of one end of the endoscope body to measure an airflow of the inspection target.

6. The diagnosis assisting endoscope system of claim 5, wherein the endoscope adaptor comprises:

an image processor connected at another end of the endoscope body, and configured to generate image data using image information acquired by the endoscope body and to extract volume data of an inspection target by analyzing the image data;

a sensor processor connected in a signal transferable form to the temperature sensor, the humidity sensor, and the airflow sensor, and configured to measure temperature data, humidity data, and airflow data in the body sensing data based on sensing values of the temperature sensor, the humidity sensor, and the airflow sensor; and a display connected in a signal transferable form to the central processor, and configured to display the disease diagnosis list about the suspected diseases of the body generated by the central processor in real time.

7. The diagnosis assisting endoscope system of claim 1, wherein the central processor is configured to transfer, to the endoscope adaptor, the first disease diagnosis list about the suspected diseases of the body generated by the central processor, and the endoscope adaptor is configured to display the first disease diagnosis list to an outside of the endoscope adaptor in real time.

8. The diagnosis assisting endoscope system of claim 1, wherein the central processor is configured to provide the body sensing data of the data storage to the endoscope adaptor, and the endoscope adaptor is configured to diagnose suspected diseases of the body in real time based on the body sensing data, and display the second disease diagnosis list about the suspected diseases of the body generated by the endoscope adaptor to an outside of the endoscope adaptor in real time.

* * * * *